United States Patent [19]

Scordato

[11] Patent Number: 4,497,774
[45] Date of Patent: Feb. 5, 1985

[54] COAGULATION INSTRUMENT FOR PERFORMING CLOTTING TESTS

[75] Inventor: Richard E. Scordato, Scarsdale, N.Y.

[73] Assignee: Medical Laboratory Automation, Inc., Mount Vernon, N.Y.

[21] Appl. No.: 473,235

[22] Filed: Mar. 8, 1983

Related U.S. Application Data

[63] Continuation of Ser. No. 275,352, Jun. 19, 1981, abandoned.

[51] Int. Cl.³ .................... G01N 35/06; G01N 33/86
[52] U.S. Cl. .......................... 422/73; 422/64; 422/67; 422/100; 436/69
[58] Field of Search .................. 422/64–67, 422/72, 73, 102, 104; 436/69; 356/39, 40, 246

[56] References Cited

U.S. PATENT DOCUMENTS

| | | | |
|---|---|---|---|
| 3,754,866 | 8/1973 | Ritchie et al. | 422/73 |
| 3,963,349 | 6/1976 | Albright et al. | 436/69 |
| 3,994,594 | 11/1976 | Sandrock et al. | 422/102 |
| 4,058,367 | 11/1977 | Gilford | 422/67 |
| 4,260,581 | 4/1981 | Sakaruda | 422/65 |
| 4,267,149 | 5/1981 | Bruckner et al. | 422/67 |
| 4,406,547 | 9/1983 | Aihara | 422/64 |

Primary Examiner—Michael S. Marcus
Attorney, Agent, or Firm—William P. Keegan

[57] ABSTRACT

A coagulation instrument for determining clotting times of plasma as an indication of various blood factors. The instrument is adapted to use three or more different reagents which are added selectively to plasma samples in accordance with a code on a cuvette in which the plasma sample is carried through the instrument. Different clotting time tests may be performed sequentially in random order as determined by the coded cuvettes.

9 Claims, 7 Drawing Figures

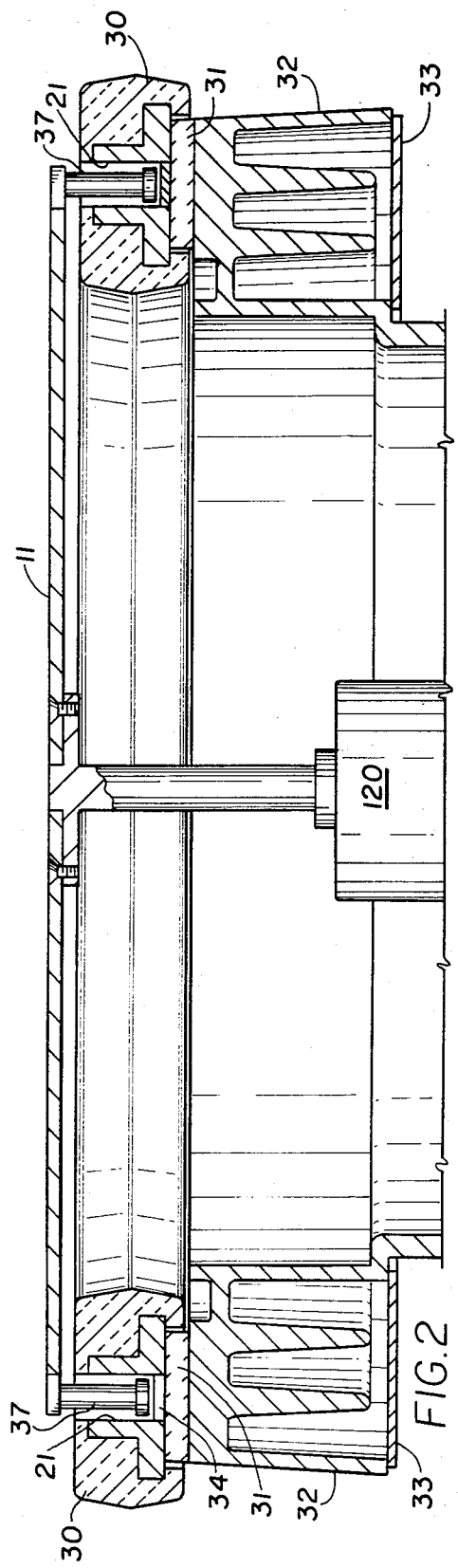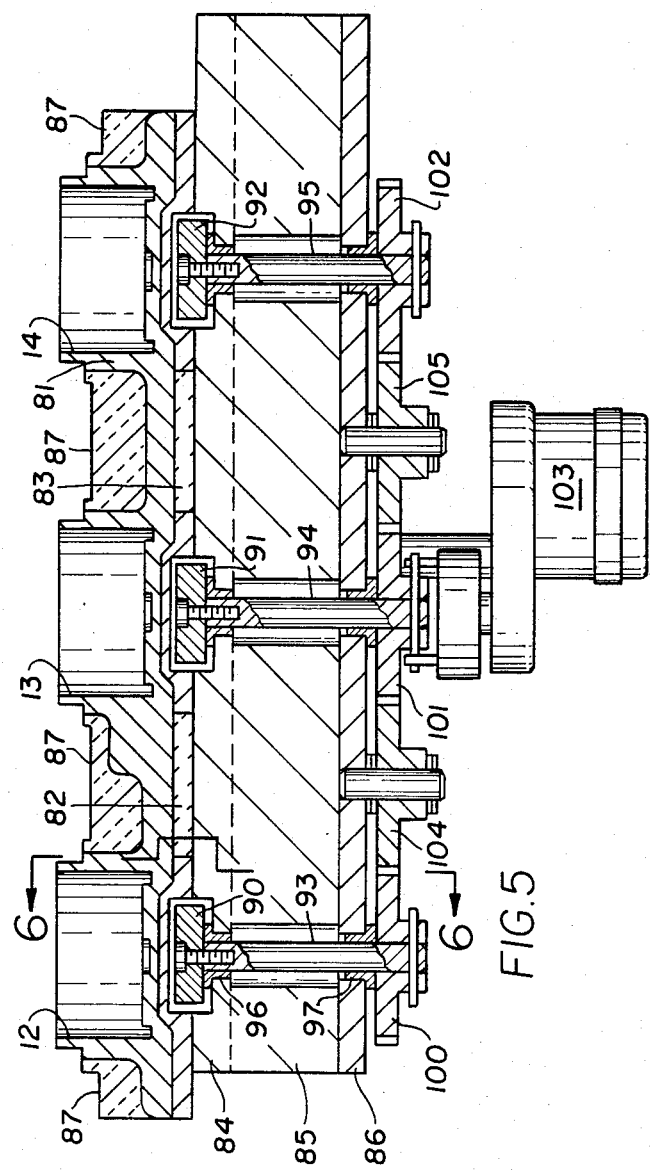

COAGULATION INSTRUMENT FOR PERFORMING CLOTTING TESTS

This is a continuation of application Ser. No. 275,352 filed June 19, 1981 abandoned.

BACKGROUND OF THE INVENTION

Automatic coagulation instruments for measuring plasma clotting times are well known in the art. For example, U.S. Pat. No. 3,607,099 discloses an instrument capable of doing the prothrombin time (PT) test serially on a plurality of plasma samples and printing the test results on a paper tape. U.S. Pat. No. 3,767,364 discloses an instrument having two reagent reservoirs from which reagents are pipetted into plasma samples. The use of two reagents facilitated testing for the activated partial thromboplastin time (APTT) of a plasma sample. U.S. Pat. No. 3,969,079 discloses an instrument that employs a dual channel cuvette disk that permits a prothrombin time test to be performed simultaneously on two plasma samples, or an APTT test to be performed simultaneously on two plasma samples, or a PT test on one plasma sample simultaneously with an APTT test on a second plasma sample. Each of the instruments disclosed in the aforementioned patents contemplated performing the same tests over and over again on plasma samples that were serially advanced to reagent dispensers and then to a test station where clot formation was determined in a clot detection circuit employing photo-optical means. When changing from one test mode to another in the instrument of U.S. Pat. No. 3,969,079, it would be necessary to replace at least one of the reagent reservoirs to go from a PT test mode to an APTT test mode, or to a PT/APTT test mode.

At the present time the APTT test represents approximately 40% of the total test load of a typical clinical laboratory. The PT test represents 50-55% of the test load, with the remainder being miscellaneous other tests. Usually, if a test is requested to determine the APTT of a patient's plasma, a test will also be requested to determine the PT as well. On the other hand, if a PT test is requested, an APTT test may not be requested. Thus, it is clear that a pattern of test requests may be random, and may not be met by instruments that are most suitable for repetitive performance of the same type test.

BRIEF SUMMARY OF THE INVENTION

Accordingly, it is the object of the present invention to provide an improved coagulation instrument that better meets the needs and demands of a typical clinical laboratory.

It is another object of the invention to provide a coagulation instrument that can randomly perform PT and APTT tests.

It is still another object of the invention to provide means for storing in an instrument under suitable conditions all the reagents that may be needed for performing tests during a day so that the required reagent may be supplied automatically to a plasma sample when a test requiring that reagent is called for by the cuvette which contains the plasma.

It is yet another object of the invention to provide an instrument that is programmed to perform various clotting time tests with the test to be performed on a plasma sample being determined by the cuvette in which the plasma is put.

It is another object of the invention to provide a coagulation instrument having separate pump means for each reagent that can be stored in the instrument ready for use when required.

In carrying out the invention, there is provided a coagulation instrument that is adapted to receive a plurality of reagent reservoirs and maintain the reagents therein in a non-deteriorating condition until such time as they are required for a clotting time test, whereupon they are automatically delivered into plasma samples. The instrument is further adapted to perform a specified test on a plasma sample in accordance with a code on the cuvette in which the plasma sample is placed. The instrument is thus provided with a plurality of cooling wells that can accommodate a plurality of reagent reservoirs and means to effect stirring of the contents of a reservoir when placed in the instrument. The instrument is further adapted to deliver reagents from two different reservoirs to a single dispensing station at which one reagent can be dispensed into a receptacle and a second reagent dispensed into a second receptacle that next reaches the dispensing station, and an additional reagent from another reservoir to another dispensing station. The instrument is provided with a code sensing station that enables it to read a cuvette code that determines the clotting time test that is to be performed on the plasma sample in the coded cuvette.

Features and advantages of the invention may be gained from the foregoing and from the description of a preferred embodiment of the invention which follows.

BRIEF DESCRIPTION OF THE DRAWINGS

FIG. 2 is a fragmentary sectional view taken along line 2—2 of FIG. 1;

FIG. 5 is a side sectional view taken through the reagent reservoir well assembly;

DETAILED DESCRIPTION OF THE INVENTION

Figure 1:
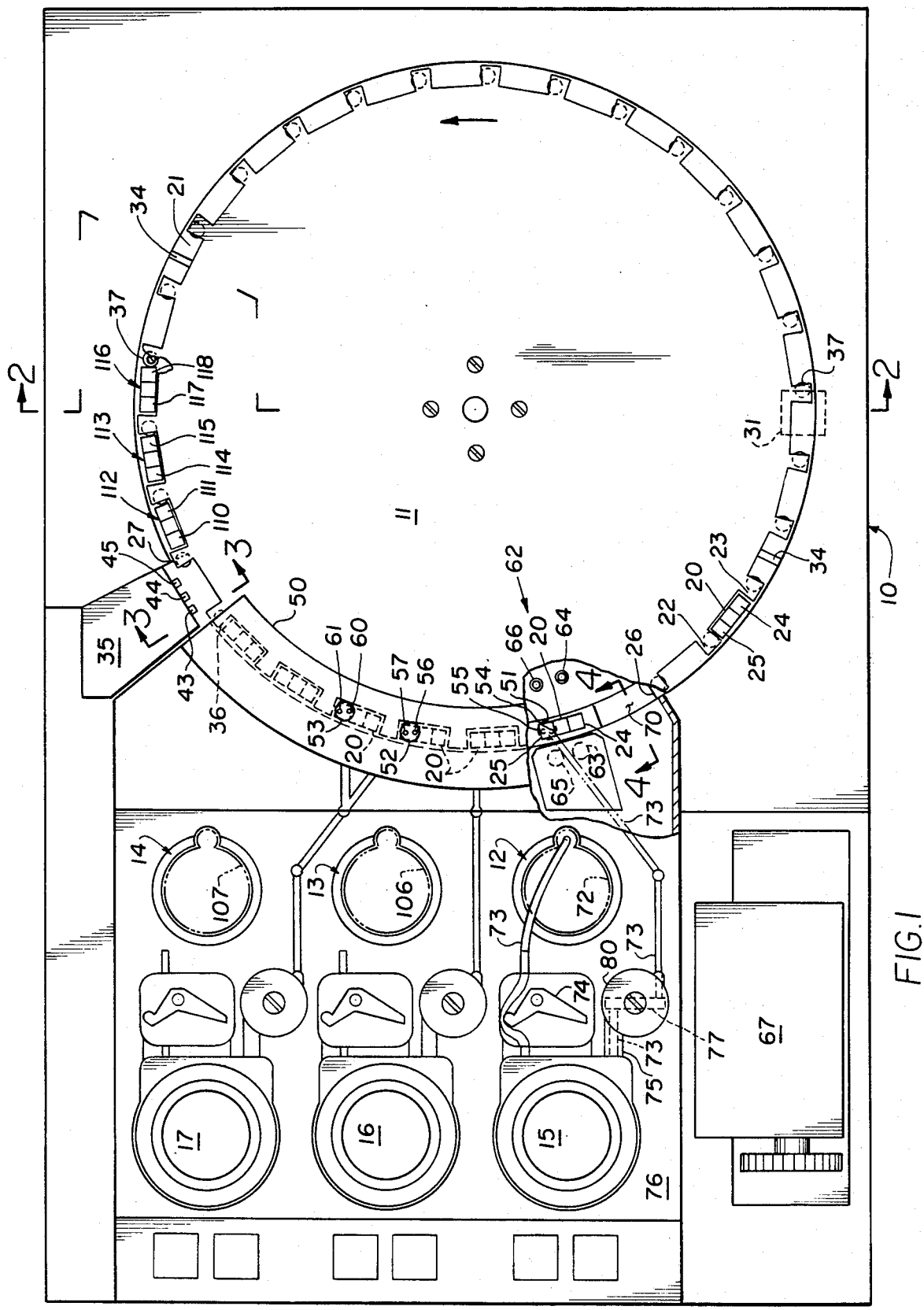
FIG. 1 is a top plan view, with parts broken away, of the coagulation instrument of the present invention.

Referring now to the drawing, and particularly to FIG. 1 thereof, the coagulation time instrument is shown generally by the reference numeral 10. It comprises a cuvette advancing mechanism 11 which is referred to as a turntable, a plurality of refrigerated or cooled reagent reservoir wells 12, 13, and 14, and a like number of pumps 15, 16, and 17 which deliver measured quantities of reagents to plasma samples for which clotting times are to be determined.

A predetermined volume of plasma will be placed in a cuvette 20 and the cuvette placed in a cooling channel 21 between two spokes 22 and 23 of turntable 11. The cuvette 20 will preferably be of the type disclosed in co-pending application Ser. No. 275,419 filed June 19, 1981 filed by Richard E. Scordato et al and entitled "Coded Cuvettes for Use in Testing Apparatus", now U.S. Pat. No. 4,371,498. It will be a dual cuvette having a pair of receptacles 24 and 25 into which plasma samples can be pipetted. Cuvette 20 will also be coded with a three station aperture code for a reason to be hereinafter described.

The cooling channel 21 is a segment of a circular machined aluminum casting extending from front end 26 to rear end 27. Channel 21 is provided with an insulated member 30 (FIG. 2) and sits on a plurality of thermo-electric cooling elements 31 spaced along its length. The warm sides of elements 31 are in contact with heat sink 32 which helps to dissipate the heat generated by elements 31. A plate 33 secured to the underside of heat sink 32 contains a current of air that is blown along the fins of the heat sink and exhausted out the back of instrument 10. Cooling channel 21 is provided with a number of drainage ports or slots 34 along its length to permit any condensation that collects in the channel to drain onto the heat sink 32 where it will be evaporated.

Since the plasma samples will be refrigerated before they are brought to the instrument for testing, they can be placed anywhere along the length of cooling channel 21 which will keep them at the proper temperature until such time as they are to have a reagent added and the mixture incubated prior to the time the clot formation is monitored. Thus, a technician can place a cuvette 20 containing plasma in each of the exposed openings of turntable 11.

The turntable 11 is indexed counter clockwise in steps to advance the cuvettes along the cooling channel towards the cuvette code sensing station 35 and thereafter to the heating block 36 which warms the plasma and the added reagent to a temperature of 37 degrees C. Each step of the turntable advances a cuvette receptacle one position to where the preceding receptacle, either the other receptacle of the same cuvette or the rear receptacle of the preceding cuvette, was. Thus, for one cuvette (in the case of dual cuvettes as disclosed herein) to be moved to a position occupied by the cuvette ahead of it requires two steps of turntable 11. It will be noted that the turntable advances the cuvettes by means of depending pusher rods 37 which, by means of their enlarged lower ends, engage the lower ends of the cuvettes. In this way, it is assured that the cuvettes will slide along cooling channel 21 with the bottoms of the cuvettes in intimate contact with the surface of the cooling channel thereby keeping the contents of the cuvettes refrigerated. In other words, the cuvettes will not be tilted with a part thereof, i.e., the rearward receptacle, out of contact with cooling channel 21 which might be the case if a cuvette were pushed at its upper end.

Figure 3:
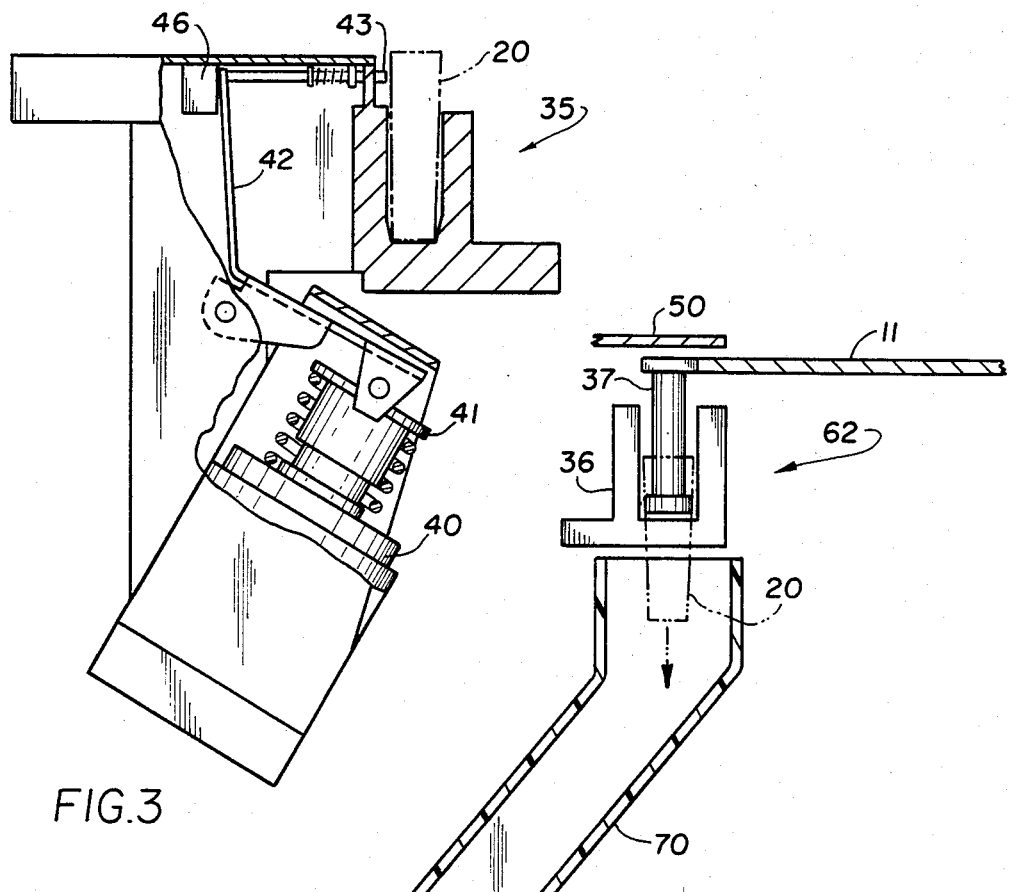
FIG. 3 is a partial sectional view taken along line 3—3 of FIG. 1.
Figure 4:
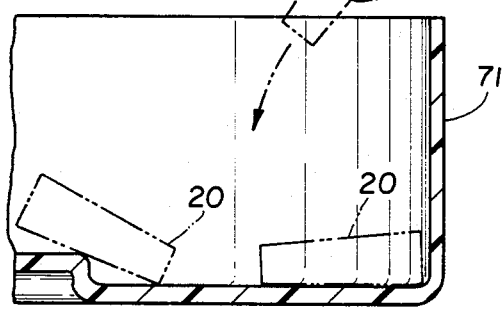
FIG. 4 is a partial sectional view taken along line 4—4 of FIG. 1.

When the turntable 11 is positioned with two adjacent spokes on opposite sides of sensing station 35, as shown in FIG. 1, solenoid 40 (FIG. 3) will be energized to attract armature 41 and pivot three leaf-spring like fingers 42 rightwardly to advance feeler pins 43, 44, and 45 towards a cuvette 20 positioned in the sensing station. If no cuvette is present, all of the pins are advanced and microswitches 46, one for each pin, actuated to indicate the absence of a cuvette. This information is stored in the instrument so that when that turntable position or station arrives at a reagent dispensing station, no reagent will be pumped through the reagent delivery system. As stated before, each cuvette 20 is coded with a three station code. Thus, one of seven different codes can be put on a cuvette, three apertures not being used since that would be the same as an absent cuvette. A particular test will be performed on the plasma in a cuvette depending on the code on the cuvette. For example, if it is desired to do a PT test on the plasma in both receptacles of a cuvette, a cuvette having a code signifying a PT test will be used for the plasma samples. When that cuvette is sensed at sensing station 35, the instrument will be programmed to add the proper reagent and perform a PT test on those particular plasma samples. If an APTT test is to be done on a plasma sample, the sample is put in a cuvette that is coded in a way to program the instrument for an APTT test. If, as in the examples just given, the same test is done on the plasma in the two receptacles of a cuvette and the plasma samples are from the same patient, the test results can be averaged for a more accurate PT or APTT determination. It sometimes happens that a PT and an APTT test are to be done for the same patient. In such a case, the two plasma samples will be put in a cuvette that is coded to program the instrument to perform a PT test on the plasma sample in one receptacle, e.g., 24, of a cuvette and an APTT test on the plasma sample in the other receptacle, e.g., 25 of the same cuvette. Since seven codes are available with a three station code, the instrument can be programmed for seven different tests or combinations of tests. With additional code stations, many more codes are available for programming the instrument for additional tests or combinations of tests.

When a cuvette 20 is advanced out of code sensing station 35 it moves to heating block 36. The block is channel shaped as cooling channel 21 but instead of being cooled, it is heated by electric heating elements to raise the plasma temperature to 37 degrees C. Since the time for turntable 11 to index one step is known, the time for a cuvette to move from the sensing station 35 to the test station is also known because it will take a certain number of turntable steps to advance from the sensing station to the test station. Thus, the incubation time can be controlled.

Over the heating block 36 is a cover plate 50 having a plurality of reagent nozzle guides 51, 52, and 53. These nozzle guides are located so that reagents, diluents, etc., can be added to the plasma samples a predetermined incubation time before the reagent/plasma mixture reaches the test station as is required in some coagulation tests. The reagent which initiates the clotting is added to the plasma at the test station. As will be described later in the specification, the reagents also will be heated before being added to the plasma samples thus assuring that the reagent/plasma mixture is at the proper temperature. It will be observed that each nozzle guide 51, 52, and 53 is provided with two apertures into which a reagent nozzle can be inserted. Guide 51 is provided with apertures 54 and 55, guide 52 with apertures 56 and 57, and guide 53 with apertures 60 and 61. The reason for this will be apparent as the description progresses.

Before referring to different reagents and different tests that can be performed in instrument 10, the path of a cuvette through the instrument will be described. When a cuvette is located below a nozzle guide, e.g., 52, a reagent dispensable through a nozzle inserted in the guide aperture, e.g., 56, may or may not be dispensed depending on how the instrument is programmed for that cuvette. Eventually, the cuvette is indexed to the test station 62 where a beam of light is directed through the reagent/plasma mixture in each receptacle. One beam of light from lamp 63 passes through the forward receptacle 24 of a cuvette and energizes the photocell 64. Similarly, a beam of light from lamp 65 passes through the rear receptacle 25 and energizes photocell 66. The photocells are connected in a clot detection circuit. Many such circuits are well known in the art and any one can be used in the present instrument.

The time that it takes a clot to form is recorded on a printed strip 67, but this component of the instrument is not a part of the present invention and will not be described. The PT and APTT (both determined by the formation of a clot and differing because different reagents are used for the two tests) are within the index time of the instrument, so a test will be completed and the results recorded before the turntable is indexed to advance the cuvettes loaded in the instrument.

In the position following the test station 62, there is no supporting track for a cuvette such as in cooling channel 21, sensing station 35, heating block 36, and test station 62. Rather, there is a dump chute 70 which delivers the cuvette containing the clotted plasma that has just been tested to a disposal bucket 71 located in the lower front part of instrument 10 where it is readily accessable for removal when loaded with expended cuvettes. The bucket itself will be mounted on its own turntable, which is driven by a take-off from the main drive (not shown, but generally a geneva mechanism) for turntable 11. The reason for providing a turntable for disposal bucket 71 is to prevent all of the cuvettes dumped through chute 70 from piling up on one side of the bucket. The fact that cuvettes are automatically removed from the supporting tracks therefor frees cooling channel 21 and turntable 11 for additional cuvettes containing fresh plasma samples to be tested. Thus, a turntable does not have to be manually emptied; the technician simply adds new cuvettes to the empty turntable positions as they appear at the front edge 26 of cooling channel 21.

Figure 6:
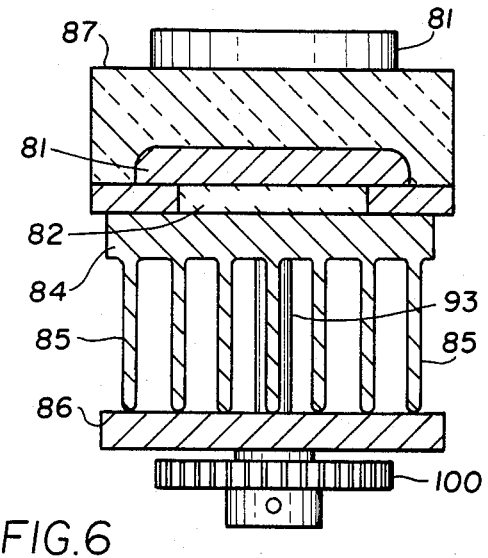
FIG. 6 is a sectional view taken along line 6—6 of FIG. 5.
Figure 7:
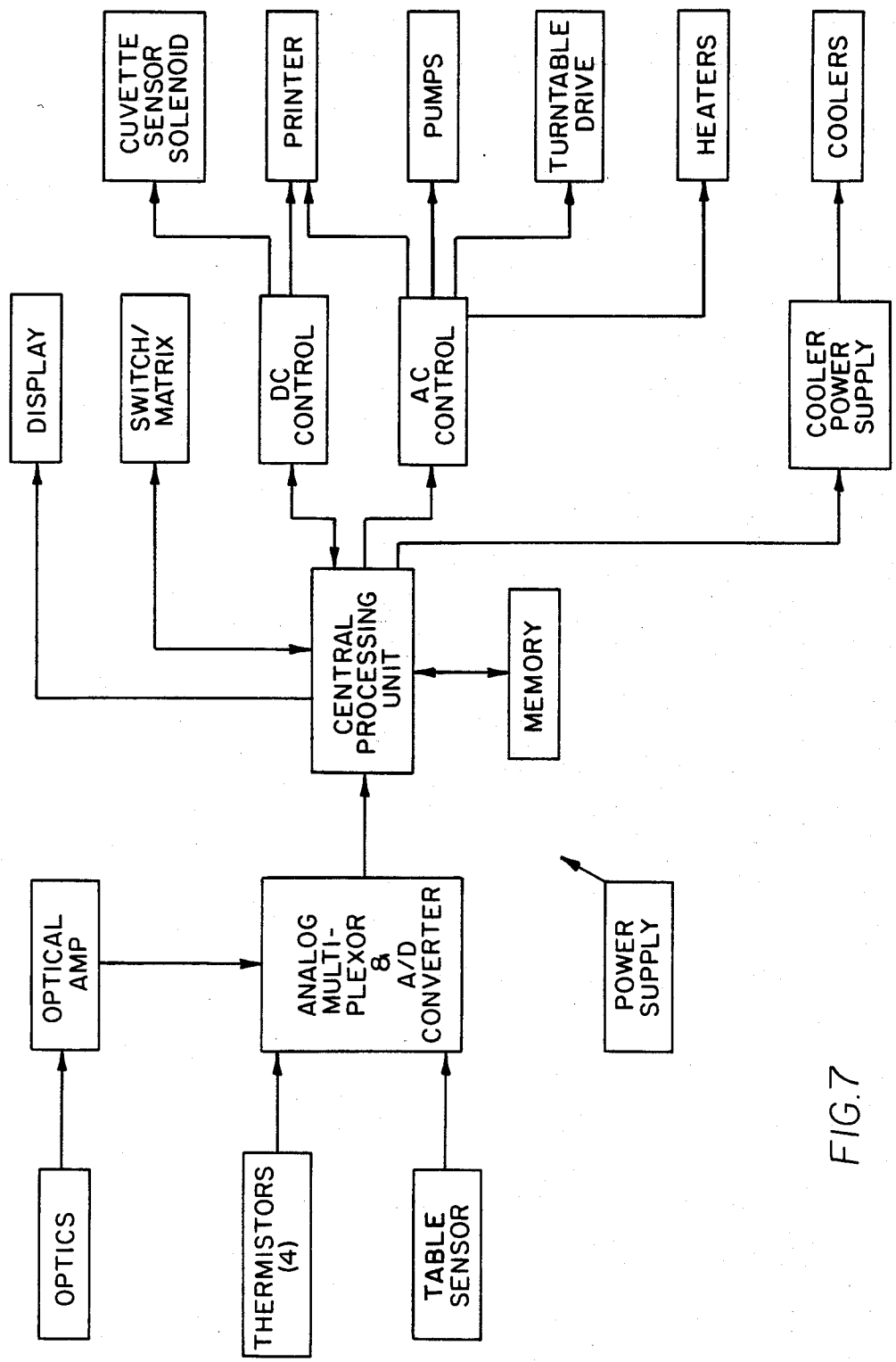
FIG. 7 is a block diagram of the instrument control circuitry.

Attention is now directed to the reagent section of the instrument, and particularly to FIGS. 1, 5, and 6. The instrument is provided with three reagent reservoir wells 12, 13, and 14 which means that three different reagents can be used or stored in the instrument. Additional reagent wells could be provided, but three have been found sufficient for the present instrument. Since each reagent well has identical associated components, only those for well 12 will be described. A reagent reservoir 72 will be positioned in well 12 and from the reservoir plastic tubing 73 will be fed past pinch valve 74 and around peristaltic pump 15 through groove 75 formed in instrument cover plate 76. A nozzle (not shown) at the end of tubing 73 will be projected downwardly through an aperture 54 in nozzle guide 51. While the particular structure of the reagent reservoir and system are not pertinent to the present invention, the reagent reservoir and tubing system disclosed in a co-pending application Ser. No. 275,420 filed June 19, 1981 filed by Richard E. Scordato et al and entitled "Reagent Reservoir System for Use in Testing Apparatus" (U.S. Pat. No. 4,367,198) is preferred. Thus, a heat exchanger 77 will be inserted in a heating unit 80 to bring the reagent to a desired temperature. If a different reservoir and tubing system is used, other arrangements can be made for heating the reagents.

The reagent wells are formed in cooling block 81 which is in contact with and cooled by thermoelectric coolers 82 and 83. The upper surface of block 81 is covered with insulating material 87 which in turn is covered by a cover plate 76 (not shown in FIG. 5). The lower side of each cooler 82 and 83, which is the warmer side, is in contact with finned heat sink 84. Heat from the sink is dissipated by blowing air through the ducts formed by fins 85 and bottom plate 86 and exhausting the air out of the instrument. Below each well 12, 13, and 14 is a rotatable bar magnet 90, 91, and 92 respectively. The magnets are mounted on shafts 93, 94, and 95, which are fitted in bushings such, for example, as 96 and 97. The ends of the shafts are keyed or pinned to gears 100, 101, and 102 which are driven by a gear reduction motor 103. Shaft 94 is driven directly, while gears 100 and 102 are driven through intermediary gears 104 and 105. The arrangement is such that when reagent reservoirs are placed in the reagent wells, and a stirring magnet is placed in each reservoir, the contents of the reservoirs can be continuously stirred by rotating magnets 90, 91, and 92. And, since the reservoirs are placed in refrigerated wells, reagents can be stored in their reservoirs directly on instrument 10 for prolonged periods of time, even when they may be used only intermittently with long periods of non-use between periods of use.

In use, and by way of example, a reservoir 72 containing calcium chloride will be placed in well 12, a reservoir 106 containing single reagent thromboplastin will be placed in well 13, and a reservoir 107 containing activator will be placed in well 14. These reagents will permit the instrument to do PT and APTT tests. The nozzle on the tubing leading from the reservoir in well 12 will be inserted through aperture 54 in nozzle guide 51. The nozzle on the tubing from the single reagent thromboplastin in reservoir 106 in well 13 will be inserted through aperture 55 in nozzle guide 51, and the nozzle on the tubing from the activator reagent in reservoir 107 in well 14 will be inserted through aperture 57 in nozzle guide 52. The tubings from the various reservoirs will be threaded around their respective pinch valves (which function in a way known in the art) and peristaltic pumps. The tubings will be primed so that upon operation of a pump, a correct volume of reagent will be dispensed through the nozzles. The volumes dispensed can be determined by the inside diameter of the tubing sections acted upon by the pumps. Motor 103 will be energized so that the contents of the several reservoirs will be stirred. The thermo-electric coolers, e.g., 31, 82, and 83 will be energized to refrigerate cooling channel 21 and reservoir wells 12, 13, and 14. Similarly, the thermo-electric heaters will be energized to warm reagent heating units 80 and plasma heating block 36. Thermistors are provided to maintain the cooling and the heating elements at the desired temperatures.

Assume that the laboratory technician receives a plasma sample for which a PT is to be determined. The correct volume of plasma is pipetted into both receptacles 110 and 111 of a cuvette 112 that is coded to program the instrument for a PT test. The cuvette 112 is placed in the cooling channel 21 in the empty space between two turntable spokes. It could be placed anywhere along the cooling channel since the channel will preserve the integrity of the plasma for a protracted period of time, but it probably would be placed in the first empty space in the turntable closet to the coding sensing station 35. It is shown in the first space adjacent to the code sensing station and is followed by other plasma filled cuvettes. Assume further that the following cuvette 113 contains plasma in receptacles 114 and 115 for which the APTT is to be determined, cuvette 113 being coded to program the instrument for that test. The next cuvette 116 in line might contain plasma in receptacles 117 and 118 that is to have both a PT and an APTT determination made for it. The PT will be measured for the plasma in the leading or first (in the direction of travel) receptacle 117 and the APTT will be measured for the plasma in the second receptacle 118. Of course, the cuvette 116 will be coded to program the instrument for a PT test and an APTT test on the two plasma samples in the one cuvette.

The instrument will then be started by actuation of the proper control button and the turntable drive mechanism 120 will be activated to index turntable 11 which advances the cuvettes in a stepwise fashion. When cuvette 112 reaches sensing station 35, solenoid 40 is energized and feeler pins 43, 44, and 45 are advanced to read the cuvette code. Micro-switches 46 are actuated as the case may be and a signal is stored in the instrument in association with cuvette that programs the instrument for a PT test on the plasma samples in receptacles 110 and 111. As the indexing of turntable 11 continues, the code on cuvette 113 will be read and a signal stored in association with cuvette that programs instrument 10 to perform APTT tests on the plasma samples 114 and 115. Similarly, when the code on cuvette 116 is read the instrument will be programmed to perform a PT test on the sample in receptacle 117 of cuvette 116 and an APTT test on the sample in the second receptacle 118 of cuvette 116. Since clotting time of the reagent plasma mixture is measured in all instances, whether the measured time is a PT or an APTT depends on the reagent that is added to the plasma sample. In other words, with certain reagents a PT will be measured, and with other reagents the measured time will be an APTT.

As turntable 11 continues to index and advance the cuvettes, cuvette 112 will pass below the nozzle in nozzle guide 52 which dispenses activator reagent, but pump 17 will not be operated and none of the reagent will be dispensed into cuvette 112. This is because pump 17 dispenses activator reagent which is used in the APTT test and not in the PT test and cuvette 112 is coded for a PT test only. However, when the receptacles 114 and 115 of cuvette 113 pass under the nozzle in nozzle guide 52, pump 17 will be operated and a required volume of activator reagent added to the plasma samples in each of receptacles 114 and 115. Under the assumptions made above, when the first receptacle of cuvette 112 is located below the nozzle from the single reagent thromboplastin reservoir 106 in well 13, which nozzle is projecting through aperture 55 in nozzle guide 51, pump 15 will be operated and a measured volume of the reagent will be added to the plasma. At the same time, the first receptacle 117 of cuvette 116 is located under the nozzle from the activator reagent reservoir 107 in well 14, but since a PT test is to be performed on that plasma sample, pump 17 is not operated, and no reagent will be dispensed into receptacle 117. At the next turntable step, the second receptacle 111 of cuvette 112 will be positioned under nozzle guide 51 and it will receive a volume of thromboplastin from reservoir 106 in well 13 because pump 16 will be operated. Since both receptacles of cuvette 112 are in test station 62 and both receptacles have received the required reagents for a PT test, lamps 63 and 65 are illuminated to shine a beam of light through the reagent-plasma mixtures in receptacles 110 and 111 of cuvette 112. Photocells 64 and 66 respond to the clot formation taking place, and the clot detection circuit responds accordingly.

At the same time that the second receptacle 11 of cuvette 112 was receiving reagent from the reservoir 106, the second receptacle 118 of cuvette 116 is located under nozzle guide 52 and it will receive a volume of activator reagent from reservoir 107 since an APTT test is to be run on the plasma sample in receptacle 118 of cuvette 116 while a PT test is to be run on the sample in receptacle 117 of the same cuvette.

As turntable 11 continues to index, receptacle 114 of cuvette 113 moves under nozzle guide 51. Since the plasma in both receptacles of the cuvette is to be tested for an APTT (the activator reagent from reservoir 107 having been dispensed into the cuvette receptacles as they stepped under nozzle guide 52) pump 15 will be operated to deliver the required volume of calcium chloride from reservoir 72. The next step of turntable 11 brings receptacle 115 of cuvette 113 under nozzle guide 51 and it too receives a measured volume of calcium chloride from reservoir 72. Both receptacles are now in test station 62 so lamps 63 and 65 are illuminated to initiate the clot detection process. The instrument printout mechanism records the APTT for each of the two samples. At this time cuvette 112 containing the previously tested plasma samples had arrived at the disposal station so it has been directed into disposal bucket 71 by chute 70.

In the example now being considered, the first receptacle 117 of cuvette 116, which contains a plasma sample that is to be tested for PT is next stepped into position under nozzle guide 51. Therefore, instrument 10 is programmed to actuate pump 16 to dispense a measured volume of thromboplastin from reservoir 106 into receptacle 117. As receptacle 118 of cuvette 116 is stepped under nozzle guide 51, the instrument is programmed to dispense a volume of calcium chloride reagent from reservoir 72 by operation of pump 15. Thus, reagents from two different reservoirs are delivered through nozzles inserted through a single nozzle guide, in this case nozzle guide 51. Both receptacles of cuvette 116 are in the test station 62 and photocells 64 and 66 react to the clot formation taking place in the receptacles. The circuitry, of which photocells 64 and 66 are a part, determine the PT and APTT of the plasma in the receptacles 117 and 118, respectively, because of the reagents added to the plasma samples. Cuvette 113 at this time has been disposed of in bucket 71. As turntable 11 continues to index, cuvette 116 will likewise be disposed of.

It is believed that the foregoing clearly demonstrates how, with different reagents in the different wells and plasma samples in differently coded cuvettes, different tests can be run on the plasma samples in random order.

If only PT is being measured, the instrument can be programmed so that the turntable indexes as soon as a clot is detected in the sample being tested. On the other hand, if a 200 second activation time is required for an APTT test, the instrument can be programmed to advance a cuvette one full position, i.e., two steps, every 100 seconds. In such a case, activator reagent will be added to the plasma at nozzle guide 52, two full positions ahead of test station 62. If a 300 second activation time is required for an APTT test, the activator reagent will be added to the plasma at nozzle guide 53, three full positions ahead of test station 62.

It should be clear that reagents other than those mentioned could be used to run clotting tests that are indicative of other blood factors. More than three reagent wells may be provided. Activation times can be adjusted by inserting a nozzle from a reagent in either nozzle guide 52 or nozzle guide 53. The nozzle from the reservoir in well 12 will generally be inserted in guide 51, while the nozzle from the reservoir 106 in well 13 may be inserted in guide 51, 52, or 53 depending on the reagent in reservoir 106 and the test being run. The nozzle from reservoir 107 in well 14 may be inserted in nozzle guide 52 or 53, again depending on the reagent being used and the test being run. Activation time can also be controlled by controlling the turntable indexing speed or the time during the cycle at which the reagent is dispensed.

Having thus described the invention it should be clear that many apparently different embodiments thereof can be provided without departing from the spirit and scope of the invention. For example, instead of coded dual receptacle cuvettes being used as described, coded single receptacle cuvettes could be used. Therefore, it is to be understood that the foregoing specification and the accompanying drawing are to be interpreted as illustrative rather than in a limiting sense.

What is claimed is:

1. A coagulation instrument adapted to randomly perform different clotting time tests on plasma samples in accordance with a test code provided on the cuvette into which a plasma sample is introduced, said instrument comprising: sensing means for reading a test code on a coded cuvette; a first dispensing station at which one or more reagents can be dispensed, said first dispensing station having guide means with a plurality of nozzle guides therein; a test station at which one or more reagents can be dispensed and at which clotting of a reagent plasma mixture is detected, said test station having guide means with a plurality of nozzle guides therein; means for moving coded cuvettes sequentially from said sensing means to said first dispensing station and thereafter to said test station; first reservoir and dispensing means adapted to dispense a reagent at said first dispensing station; first pump means for delivering a predetermined volume of reagent from said first reservoir means at said first dispensing station; second reservoir and dispensing means adapted to dispense a reagent at said first dispensing station or at said test station; second pump means for delivering a predetermined volume of reagent from said second reservoir means at said first dispensing station or at said test station; third reservoir and dispensing means adapted to dispense a reagent at said test station; third pump means for delivering a predetermined volume of reagent from said third reservoir means at said test station; said first, second, and third dispensing means each having separate dispensing nozzles with said first dispensing nozzle being adapted to be connected to and cooperate with the first dispensing station guide means, the second dispensing nozzle being adapted to be connected to and cooperate with the first dispensing station guide means or the test station guide means, and the third dispensing nozzle being adapted to be connected to and cooperate with the test station guide means; circuit means responsive to the dispensing of a reagent into a plasma sample at said test station for detecting clot formation in the reagent plasma mixture and for measuring the time period between reagent dispensing at said test station and clot formation; and means responsive to the code sensed on a coded cuvette by said sensing means for controlling said first pump means to either dispense or not dispense a reagent to a cuvette from said first reservoir means when the cuvette is moved to said first dispensing station and for controlling said second pump means to either dispense or not dispense a reagent to a cuvette from said second reservoir means when the cuvette is moved to said first dispensing or test station depending on which station guide means the second dispensing nozzle is connected to and for controlling said third pump means to dispense a reagent from said third reservoir means when a cuvette is moved to said test station, the arrangement being such that when reagents are added to a cuvette at said first dispensing station and at said test station in response to the code on the cuvette an APTT test or a double reagent PT test is performed and when a reagent is added to a cuvette only at said test station in response to the code on the cuvette a single reagent PT test is performed.

2. A coagulation instrument according to claim 1 wherein said sensing means includes means for reading a test code on a dual receptacle coded cuvette, and wherein said circuit means includes means for detecting clot formation in each receptacle of said cuvette, and wherein said means responsive to the code on a cuvette for controlling the pump means includes means to dispense a reagent or reagents into both receptacles of the cuvette so that the same test is performed on the reagent plasma mixtures in each receptacle of the cuvette or that different tests are performed on the reagent plasma mixtures in each receptacle.

3. A coagulation instrument according to claim 1 including disposal means by which cuvettes are removed from said cuvette moving means and deposited in a waste container after a reagent plasma mixture therein has been tested.

4. A coagulation instrument according to claim 2 including disposal means by which cuvettes are removed from said cuvette moving means and deposited in a waste container after a reagent plasma mixture therein has been tested.

5. A coagulation instrument according to claim 1 wherein the cuvette moving means comprises stepping means for advancing the cuvettes at a predetermined stepping rate, said stepping rate having a time period greater than the time period of clot formation.

6. A coagulation instrument according to claim 1 including a second dispensing station at which one or more reagents can be dispensed, said second dispensing station having guide means with a plurality of nozzle guides therein, and wherein said first dispensing nozzle is adapted to be connected to and cooperate with said first or said second dispensing station guide means, and wherein said second dispensing nozzle is adapted to be connected to and cooperate with said first or said second dispensing station guide means or said test station guide means.

7. A coagulation instrument according to claim 6 wherein a dispensing nozzle is connected to and cooperates with the first dispensing station when a first predetermined reagent activator time is required for a plasma reagent mixture, and is connected to and cooperates with the second dispensing station when a second predetermined reagent activator time is required for the plasma reagent mixture.

8. A coagulation instrument according to claim 6 wherein the cuvette moving means comprises stepping means for advancing the cuvettes at a predetermined stepping rate, said stepping rate having a time period greater than the time period of clot formation.

9. A coagulation instrument according to claim 6 including disposal means by which cuvettes are removed from said cuvette moving means and deposited in a waste container after a reagent plasma mixture therein has been tested.

* * * * *